US006343127B1

(12) United States Patent
Billoud

(10) Patent No.: US 6,343,127 B1
(45) Date of Patent: Jan. 29, 2002

(54) ACTIVE NOISE CONTROL SYSTEM FOR CLOSED SPACES SUCH AS AIRCRAFT CABIN

(75) Inventor: Guy D. Billoud, Apex, NC (US)

(73) Assignee: Lord Corporation, Cary, NC (US)

( * ) Notice: Subject to any disclaimer, the term of this patent is extended or adjusted under 35 U.S.C. 154(b) by 931 days.

(21) Appl. No.: 08/533,227

(22) Filed: Sep. 25, 1995

(51) Int. Cl.[7] .......................... A61F 2/20; G10K 11/16; H03B 29/00

(52) U.S. Cl. ..................................... 381/71.4; 381/71.7

(58) Field of Search ............................ 381/71, 94, 86, 381/88, 77, 90, 188, 71.1, 71.2, 71.3, 71.4, 71.7; 351/FOR 123; 415/119

(56) References Cited

U.S. PATENT DOCUMENTS

| | | | | | |
|---|---|---|---|---|---|
| 2,776,020 | A | * | 1/1957 | Conover et al. | 381/77 |
| 3,945,461 | A | | 3/1976 | Robinson | 181/153 |
| 4,153,815 | A | | 5/1979 | Chaplin et al. | 179/1 P |
| 4,356,881 | A | | 11/1982 | Lowell | 181/150 |
| 4,562,589 | A | * | 12/1985 | Warnaka et al. | 381/71 |
| 4,567,959 | A | * | 2/1986 | Prophit | 381/86 |
| 4,620,317 | A | | 10/1986 | Anderson | 381/90 |
| 4,689,821 | A | | 8/1987 | Salikuddin et al. | 381/71 |
| 4,715,559 | A | | 12/1987 | Fuller | 381/71 |
| 5,024,288 | A | | 6/1991 | Shepherd et al. | 181/206 |
| 5,115,884 | A | | 5/1992 | Falco | 181/156 |
| 5,123,500 | A | | 6/1992 | Malhoit et al. | 181/144 |
| 5,173,943 | A | | 12/1992 | Dzurko | 381/98 |
| 5,245,664 | A | | 9/1993 | Kinoshite et al. | 381/71 |
| 5,257,316 | A | | 10/1993 | Takeyama et al. | 381/71 |
| 5,400,408 | A | * | 3/1995 | Lundgren et al. | 381/88 |
| 5,410,605 | A | | 4/1995 | Sawada et al. | 381/71 |
| 5,426,703 | A | | 6/1995 | Hamabe et al. | 381/71 |
| 5,526,292 | A | | 6/1996 | Hodgson et al. | 364/574 |

* cited by examiner

*Primary Examiner*—Xu Mei
(74) *Attorney, Agent, or Firm*—Randall S. Wayland

(57) ABSTRACT

An active noise control system (20) which generates via an electronic controller (22) a canceling signal(s) which are responsive to a signal from an error sensor(s) (28) to drive a speaker (30) or array of speakers. Each speaker (30) is contained within an enclosure (33) and is inversely and rigidly mounted therein. The enclosure (33) attaches to the trim panels (25) attached to the closed structure (34) and the canceling sound wave form is directed primarily toward the interior surface (36) of the trim (25). Preferably, the speaker (s) (30) are flexibly suspended with mounts (38) to the trim (25). The enclosure (33) preferably includes planar wave guide means such as escapeways (40) for initially directing the canceling sound wave form (anti-noise) in a plane substantially parallel to the surface of the trim (25).

18 Claims, 5 Drawing Sheets

ACTIVE NOISE CONTROL SYSTEM FOR CLOSED SPACES SUCH AS AIRCRAFT CABIN

FIELD OF THE INVENTION

The present invention is directed to active noise control. More particularly, this invention is an active noise control system for canceling or reducing unwanted noise in a closed space.

BACKGROUND OF THE INVENTION

Active noise control systems are known which use an inverse-phase sound wave to cancel a disturbance. U.S. Pat. No. 4,562,589 to Warnaka et al. entitled "Active Attenuation of Noise in a Closed Structure" teaches a system for active attenuation of noise within a closed structure such as an aircraft cabin which operates to introduce a canceling sound wave form (anti-noise) into a closed structure which is responsive to an error signal. The system includes an adaptive filter for updating the cancellation signal sent to the transducers (speakers) to produce the canceling wave form. Although this system was a phenomenal advance for its time, it is somewhat inefficient at reducing noise within the closed space. Furthermore, the components are subject to damage upon large impact loads.

SUMMARY OF THE INVENTION

In light of the advantages and drawbacks to the prior art, the present invention is directed to active noise control system for reducing noise within a closed space caused by a source of disturbance such as from a noise and/or vibration source. More particularly, this invention is an efficient active noise control system comprising a reference sensor for deriving a reference signal indicative of a source of disturbance which causes a disturbing noise to be produced in the closed space, an error sensor for sensing a residual sound pressure level and providing a signal indicative thereof to an electronic controller. The electronic controller includes an adaptive filter for providing a canceling signal to a speaker for generating a canceling wave form. The canceling wave form endeavors to cancel the noise caused in the closed space by the source of disturbance. In the present invention, the speakers are inverted in their enclosures and attached directly to the trim of the closed space, thus, providing for more efficient noise cancellation. Preferably, the enclosures are soft-mounted by elastomer isolators or mounts to protect the speaker components from damage to transient loads applied thereto. Each enclosure assembly and installation preferably performs the function of a planar wave guide and constrains the canceling wave form such that it emanates from the confines of the enclosure in a direction which is substantially parallel to the trim's surface. Further inventive features of the present invention will be apparent from the following detailed description, claims and drawings.

BRIEF DESCRIPTION OF THE DRAWINGS

The accompanying drawings which form a part of the specification, illustrate several key embodiments of the present invention. The drawings and description together, serve to fully explain the invention. In the drawings.

DETAILED DESCRIPTION OF THE PREFERRED EMBODIMENT

Figure 1:
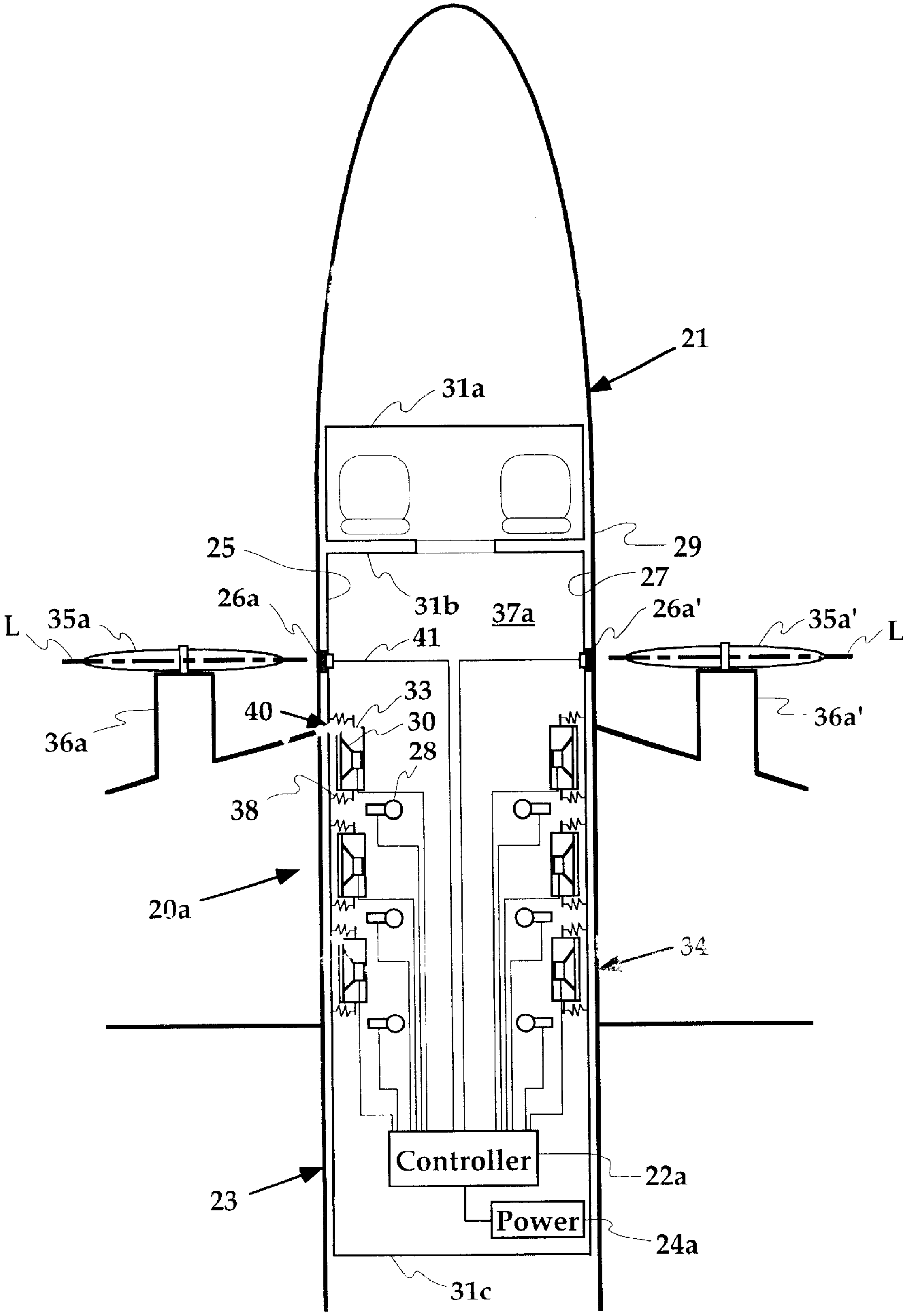
FIG. 1 is a schematic depiction of an embodiment of the active noise control system of the present invention in a propeller-driven aircraft.

A schematic depiction of an embodiment of the active noise control system of the present invention is shown in FIG. 1 generally at 20*a*. It should be noted that when comparing the various embodiments that like numerals have been used to denote like elements. The system 20*a* is shown with reference to an aircraft application. However, it should be understood that the system 20*a* will operate in any closed space to reduce unwanted noise within. The aircraft shown in this embodiment is a propeller driven aircraft and includes a fuselage 34 having a nose section 21, an aft section 23, and interior surface 27 and exterior surface 29. Interior surface 27 has trim 25 attached thereto by fasteners, adhesive or the like. The trim 25 includes bulkheads 31*a*, 31*b*, 31*c* and floor 32 (similar to that shown in FIG. 2) and defines and forms the closed space of the aircraft cabin 37*a*. The closed space is generally where the human occupants are resident. It is, therefore, for this reason that a quite environment is desired.

In this embodiment, the propellers 35*a* and 35*a*' are driven by engines 36*a* and 36*a*' and cause propeller wash to impinge on the exterior surface 29 of the fuselage 34 along the plane of action indicated by lines L and generate a sound pressure level within the aircraft cabin 37*a*. The system 20*a* includes means for deriving a reference signal indicative of the disturbance which is causing the unwanted noise in the closed space. In this case, two reference signals are used and the reference signals are derived from reference sensors 26*a* and 26*a*'. These sensors 26*a* and 26*a*' are preferably accelerometers that are placed on or directly adjacent the interior surface 27 of the fuselage 34 in the plane of action of the propeller wash. Alternatively, microphones may be used. Reference sensors 26*a* and 26*a*' should be placed at a point where the propeller wash disturbance of the fuselage 34 is the greatest.

In general, since the predominant tone to be canceled in the closed space in a propeller driven aircraft is the BPF (standing for Blade Pass Frequency) tone caused by the propeller wash impinging on the exterior surface 29 of the fuselage 34, the BPF tone is what is needed for the reference signal. In other embodiments, other reference signals such as tachometer signals, engine signals indicative of the rotating speed, or other signals indicative of the noise may be required. The key is that the reference signal be indicative of the phase relationship and frequency of the disturbance. Depending on the control method used, the magnitude or frequency of the reference signal may also be important. In this embodiment, the reference signal is directed to electronic controller 22*a* via wire lead 41. The reference signal may be band-pass filtered, high pass filtered, or low pass filtered, used directly or used to trigger a wave form generator. The conditioning of the signal will depend on the type of filtering and control method used. Power 24*a* is preferably supplied by the aircraft's resident power supply.

The system 20*a* in this embodiment includes a series of speaker assemblies 50. A description will be detailed as to one assembly 50 only. Other assemblies 50 are preferably similar in makeup. The system 20*a* includes speaker means for generating a canceling wave form for reducing the residual sound pressure level within the aircraft cabin 37*a*. Typically, the control will concentrate on one or more dominant and annoying tones. As a goal, the tonal noise would be completely eliminated, however, usually this is not obtainable, thus, it is realistically desirable to globally reduce the sound pressure level in the aircraft cabin 37*a* to a minimum.

In one novel aspect of the present invention, the speaker 30 is rigidly attached to a enclosure 33 by fasteners or the like. The enclosure 33, which is preferably box like, is then inversely-mounted relative to the trim 25 such that the canceling wave form is primarily and substantially directed at the surface of the trim 25 adjacent the enclosure 33. This is termed being "inverted" within the enclosure. Prior art active noise control systems for aircraft have directed the canceling noise directly into the cabin. The inversion of the speaker 30 is thought to increase the reverberation of the speaker assembly 50. This is particularly desired for controlling low-frequency noise such as is experienced in propeller-driven aircraft. Low frequency would be considered in the range of between 20 Hz and 400 Hz. Preferably, the enclosure 33 is attached to the trim 25 such as aft bulk head 31*c*, mid bulkhead 31*b* or to floor 32 (FIG. 2) by mounts 38. These can be shear-type mounts, sandwich mounts or the like. Preferably, the mounts 38 are elastomeric and act in either shear or compression with preferable stiffness ranges between about 0.5 lb./in. and 15 lb./in. Preferably, four elastomer mounts 38 are used to attach each enclosure 33 to the trim 25.

The enclosure 33, preferably, includes planar wave guide means in the form of multiple escapeways 40 formed between the trim 25 and the enclosure 33 to direct the escape of canceling wave form as it escapes from the enclosure 33 to be initially in a direction substantially parallel to the surface of trim 25. Preferably, these escapeways 40 are formed by mounts 38 spacing the enclosure 33 away from the trim 25. Soft-mounting of the enclosure 33 protects the components in the speaker 30 from shock loads and avoids unwanted vibration from the speaker to be transmitted to the structure.

An error sensor 28, and preferably an array of error sensors are strategically located within the aircraft cabin to allow the control such as least means square (LMS) control to produce a quiet zone adjacent the passengers' heads. The error signal derived from the error sensor 28 is indicative of the sound pressure level at the location of the error sensor. Various averaging schemes can be used when arrays of sensors are used. The error signal is used by an electronic controller 22*a* and produces a canceling wave form in the form of anti-noise (180° out of phase) to reduce the noise at the location of the error sensor 28. If an array of sensors are used, such as in most aircraft systems, the control will seek to globally reduce and minimize the sound pressure level within the aircraft cabin 37*a*.

Figure 2:
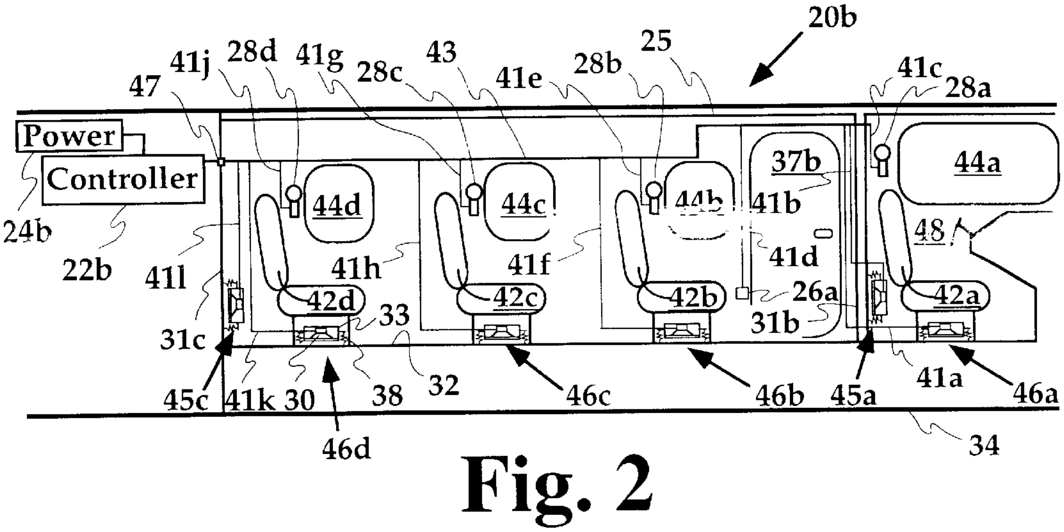
FIG. 2 is a side view, schematic depiction of an embodiment of the active noise control system illustrating under seat and inverse mounting of the speaker assemblies.

FIG. 2 illustrates a side view of another embodiment of active noise control system 20*b* for noise reduction in an aircraft cabin 37*b*. Illustrated are the floor-mounted speaker assemblies 46*a*, 46*b*, 46*c*, and 46*d* wherein the enclosures 33 are attached, and preferably soft-mounted to the floor 32 beneath the seats 42*a*, 42*b*, 42*c*, and 42*d* by mounts 38. The installation is shown with the electronic controller 22*b* positioned behind the rear bulkhead 31*c* in the unpressurized portion of the aircraft. All leads 41*a* through 411 from the speakers 30, error sensors 28*a*, 28*b*, 28*c*, and 28*d* and reference sensors 26*a* are collected into a wire bundle 43 which is connected to the electronic controller 22*b*. A sealed connector 47 is used to traverse through the aft bulkhead 31*c*.

In the FIG. 2 embodiment, the error sensors 28*a*, 28*b*, 28*c*, and 28*d*, preferably microphones, are installed adjacent the trim 25, and preferably, directly adjacent the windows 44*a*, 44*b*, 44*c*, and 44*d*. The trim 25 is directly attached to the fuselage 34. A wall-mounted speaker assembly 45*a*, which in this case is bulkhead mounted, is illustrated installed in the cockpit 48 of the aircraft and attached to the mid or partition bulkhead 31*b*. Similarly, a wall-mounted speaker assembly 45*c* is mounted on an aft bulkhead 31*c*. In a similar fashion, a wall-mounted speaker assembly could be mounted on the partition bulkhead 31*b* and directed toward the passengers.

Figure 3:
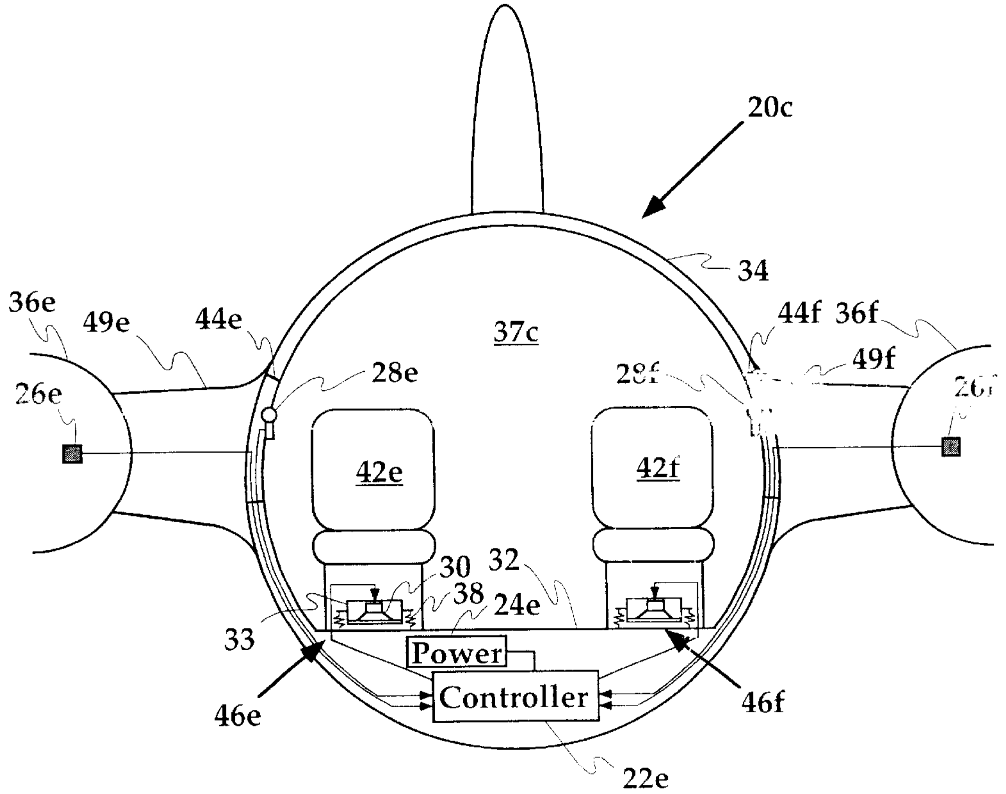
FIG. 3 is a frontal view, schematic depiction of another embodiment of the active noise control system illustrating reference sensors adjacent the jet engines and error sensors adjacent the interior trim.
Figure 4:
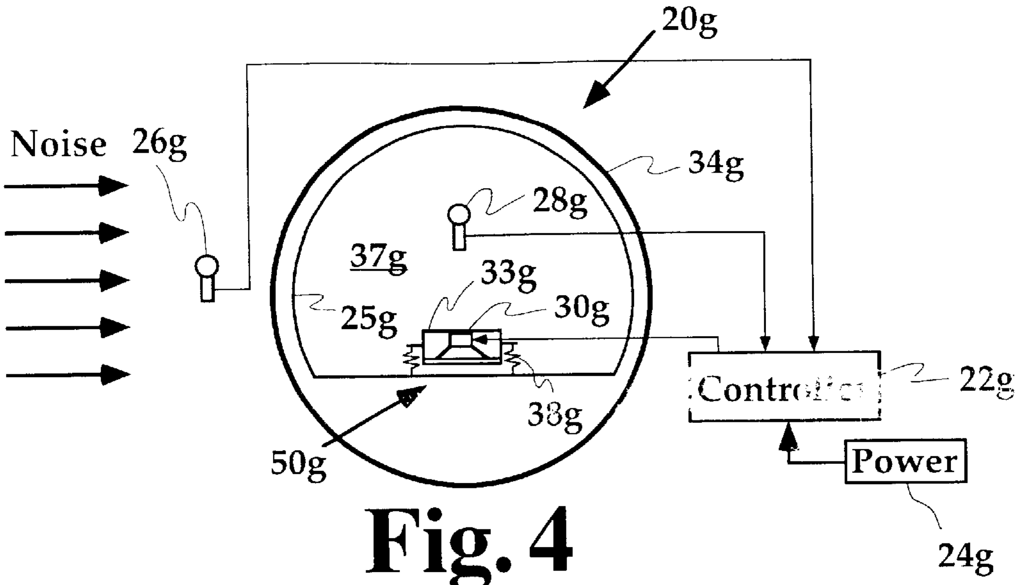
FIG. 4 is a schematic depiction of another embodiment of active noise control system using a reference sensor located outside the closed space which receives far-field noise from a source of noise disturbance.
Figure 5:
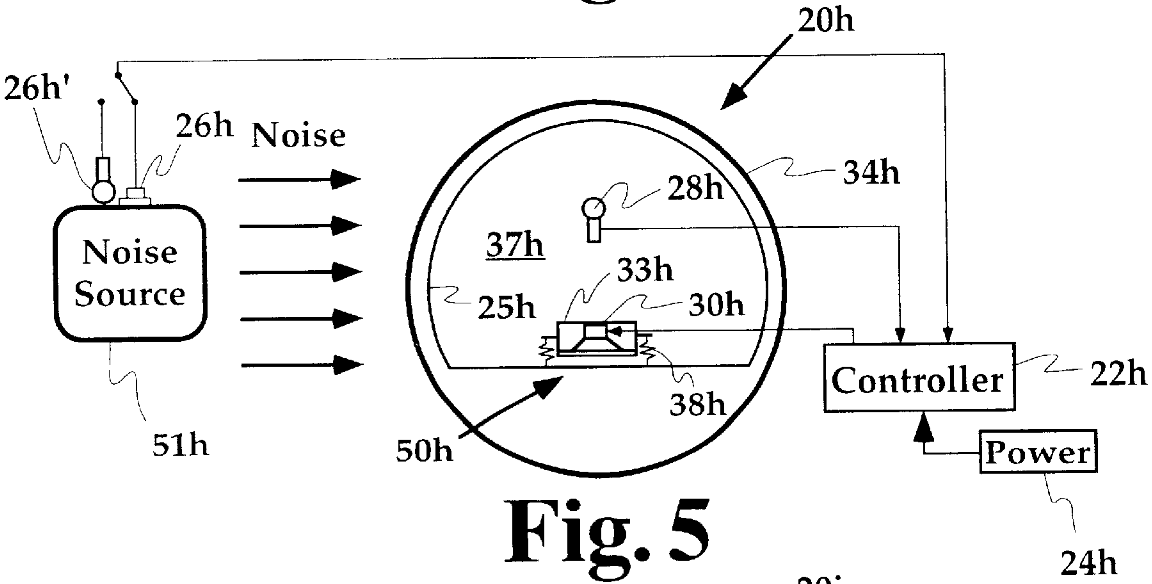
FIG. 5 is a schematic depiction of another embodiment of active noise control system using a reference sensor directly adjacent the noise source which is outside the closed space.
Figure 6:
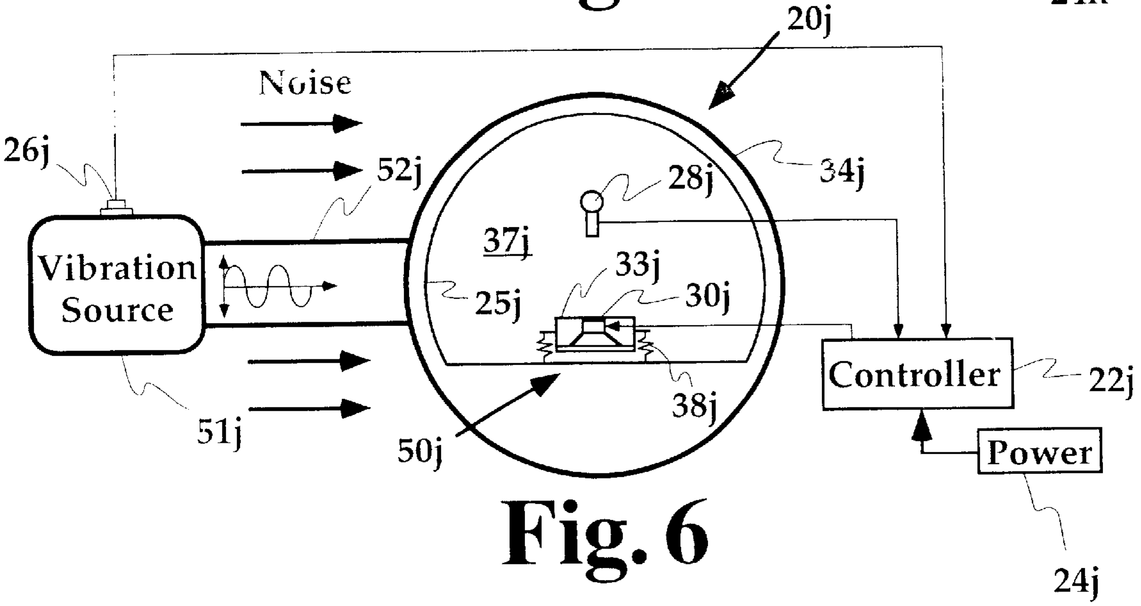
FIG. 6 is a schematic depiction of another embodiment of active noise control system using a sensor for deriving a reference signal indicative of a vibration emanating from vibration source where the vibration source causes a noise to develop in the closed space.

FIG. 3 illustrates an aft-looking view of another embodiment of active noise control system 20*c* for a jet-engine aircraft which uses floor-mounted speaker assemblies 46*e* and 46*f*. The speakers 30 in the assemblies 46*e* and 46*f* are inversely-mounted in the enclosures 33 underneath the seats 42*e* and 42*f* such that the canceling sound wave form is directed substantially toward the floor 32. Preferably the enclosures 33 are mounted to the floor by mounts 38. Error sensors 28*e* and 28*f* are located in the trim adjacent the windows 44*e* and 44*f*. The reference sensors 26*e* and 26*f* are taken from the engines 36*e* and 36*f*, such as turbofan jet engines, to provide reference signals that are indicative of the vibration of the engines 36*e* and 36*f* that imparts noise and vibration to the fuselage 34 through struts 49*e* and 49*f*. The vibration causes unwanted noise in the aircraft cabin 37*c*. The electronic controller 22*e* and power supply 24*e*, in this embodiment, are shown mounted under the floor 32, but could be mounted at any convenient location FIGS. 4, 5, and 6 schematically depict various systems 20*g*, 20*h*, and 20*j* and closed spaces 37*g*, 37*h*, and 37*j* where there is unwanted noise therein to be reduced. Each includes an electronic controller 22*g*, 22*h*, and 22*j* which includes a memory and a digital signal processor (DSP) which is used to execute a control algorithm such as LMS or the like to minimize unwanted noise within the closed spaces 37*g*, 37*h*, and 37*j*. Each closed space spaces 37*g*, 37*h*, and 37*j* includes a speaker assembly 50*g*, 50*h*, and 50*j* which include speakers 30*g*, 30*h*, and 30*j* and enclosures 33*g*, 33*h*, and 33*j*. The speakers 30*g*, 30*h*, and 30*j* are inversely-mounted in the enclosures 33*g*, 33*h*, and 33*j* such that the canceling wave form is directed substantially toward the trim 25*g,* 25*h,* and 25*j*. In these embodiments, floor mounted versions are shown, but wall mounting is envisioned as well. Further, the speaker enclosures 33*g,* 33*h,* and 33*j* are soft-mounted to the trim 25*g,* 25*h,* and 25*j* by mounts 38*g,* 38*h,* and 38*j*.

Illustrated are four types of reference sensors 26*g,* 26*h,* 26*h*', and 26*j* which are used to derive a signal indicative of the frequency, and/or phase, and/or magnitude of the disturbance noise and/or vibration source. Reference sensor 26*g* picks up noise and generates a signal indicative of the noise in the far-field which is causing unwanted noise in the closed space 37*g*. Reference sensor 26*h* and optionally 26*h*' pick up noise (and optionally mechanical vibration) generated by a noise source 51*h* and generate a signal indicative of the noise generated by the source 51*h* which is causing an unwanted noise in the closed space 37*h*. The signal may be generated by either an accelerometer or a microphone. Further, a tachometer signal may be used. Similarly, reference sensor 26*j* picks up vibration generated by a vibration source 51*j* such as an engine which is directly attached to the closed space 37*f* by a connecting structure 52*j*. The vibration and noise causes an unwanted noise in the closed space 37*j*. Error sensors 28*g,* 28*h,* and 28*j* are used to derive a signal indicative of the residual noise pressure level in the closed spaces 37*g,* 37*h,* and 37*j*. Each of these systems 20*g,* 20*h,* and 20*j* are efficient systems for reducing unwanted noise, and in particular they are efficient for reducing noise in the frequency range between about 20 Hz and 800 Hz.

Figure 7:
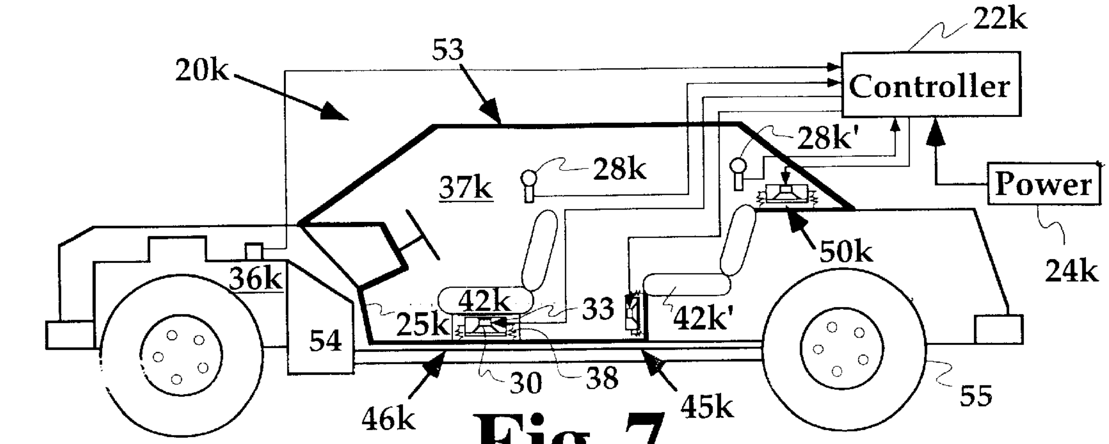
FIG. 7 is a schematic depiction of another embodiment of active noise control system operating in the environment of an automobile passenger compartment.

FIG. 7 illustrates the present invention active noise control system 20*k* used in the environment of a vehicle such as an automobile. The vehicle 53 includes an engine 36*k,* and a transmission 54 for driving wheels 55 or the like. The active noise control system 20*k* operates to reduce interior noise due to the engine 36*k* which causes unwanted noise in the passenger compartment 37*k*. Speaker assemblies 45*k,* 46*k,* and 50*k* mount to the trim 25*k* such as underneath seats 42*k,* on the window platform, or in the front of the rear seat 42*k*' or the like. Each speaker assembly is mounted to the trim 25*k* by mounts 38 and speakers 30 inversely-mounted in the enclosure 33. At least one error sensor 28*k* is included in the closed space 37*k*. Preferably, multiple sensors such as 28*k* and 28*k*' are used in the areas where localized quiet zones are desired.

Figure 8:
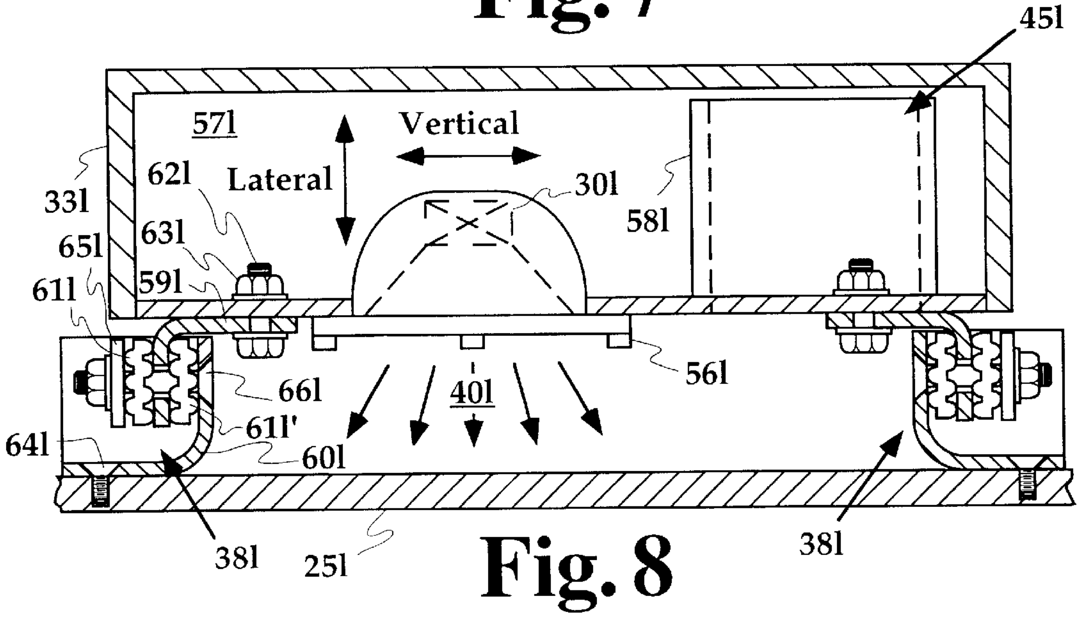
FIG. 8 is a schematic depiction of an inversely-mounted speaker system that includes grommet-type mounts and a wall mounted orientation.

FIG. 8 illustrates a wall-mounted speaker assembly 451 including acoustic speaker 301 which is rigidly attached to an enclosure 331 by fasteners 561 or the like. The enclosure preferably includes an interior volume 571 and a low-frequency reflex port 581. Speaker 301 is preferably offset to one corner of the enclosure 331 to reduce the acoustic loading on the speaker 301. The enclosure 331 attaches to the trim 251 by way of mounts 381. In this embodiment, grommet-type mounts are used. The mounts 381 include means for attaching to the enclosure 331 such as a first bracket 591, bolt 621 and nut 631. The mounts 381 also include means for attaching to the trim 251 such as second bracket 601 and screw 641. Flexing elements 611 and 611' such as grommets are compressed between first bracket 591 and second bracket 601, and similarly, between first bracket 591 and washer 651 by torqueing fastener 661. Grommets are compressed enough such that they allow for flexible relative movement between the enclosure 331 and the trim 251 without slippage. Preferably, the grommets are loaded in compression under vertical gravity loading.

Figure 9:
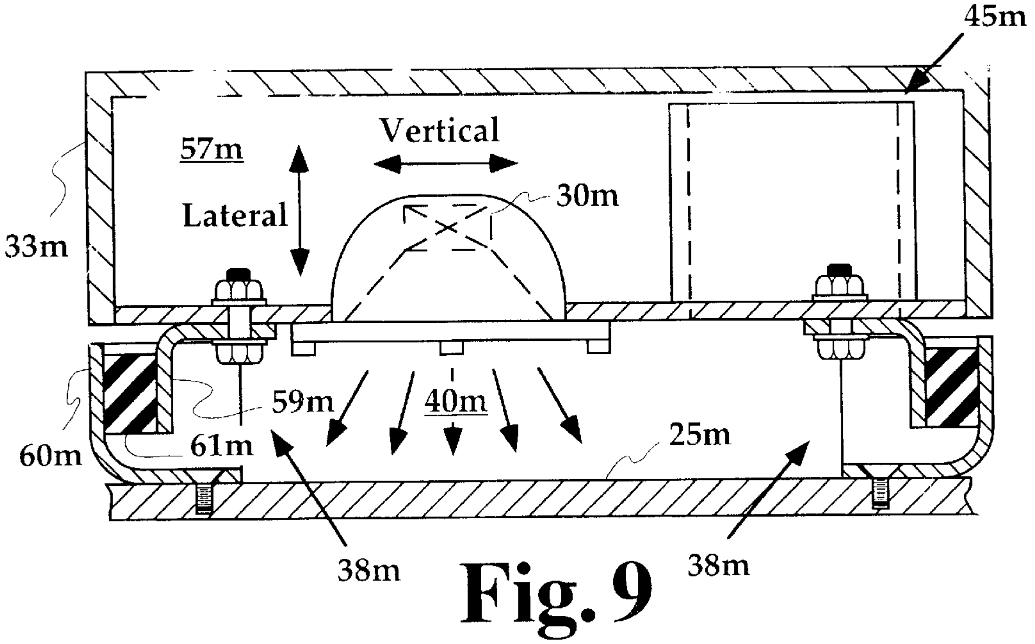
FIG. 9 is a schematic depiction of an inversely-mounted speaker system that includes shear-type mounts in a wall mounted orientation.

FIG. 9 depicts another type of mount 38*m* for flexibly mounting the enclosure 33*m* to the trim 25*m*. The mounts 38*m* are bonded compression mounts. Each includes a first bracket 59*m* for attachment to the enclosure 33*m* and a second bracket 60*m* for attachment to the trim 25*m* and a flexing element 61*m* bonded therebetween. For this wall-mounted assembly, it is desired that the flexing element 61*m* be elastomer such as natural rubber and be loaded in direct compression.

Figure 10:
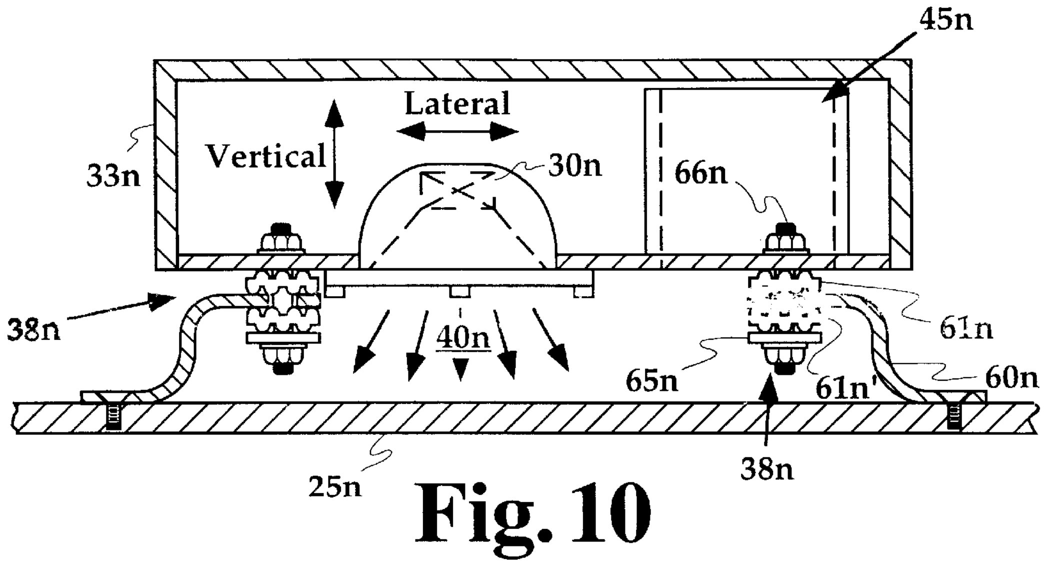
FIG. 10 is a schematic depiction of an inversely-mounted speaker system that includes grommet-type mounts in a floor mounted orientation.

FIG. 10 depicts floor-mounting the enclosure 33*n* of the speaker assembly 45*n* with grommet-type mounts 38*n* for flexibly mounting the enclosure 33*m* to the trim 25*m*. Each mount 38*n* includes a bracket 60*n* a washer 65*n,* and flexing elements 61*n* and 61*n*'. Torqueing fastener 66*n* properly precompresses flexing elements 61*n* and 61*n'*.

Figure 11:
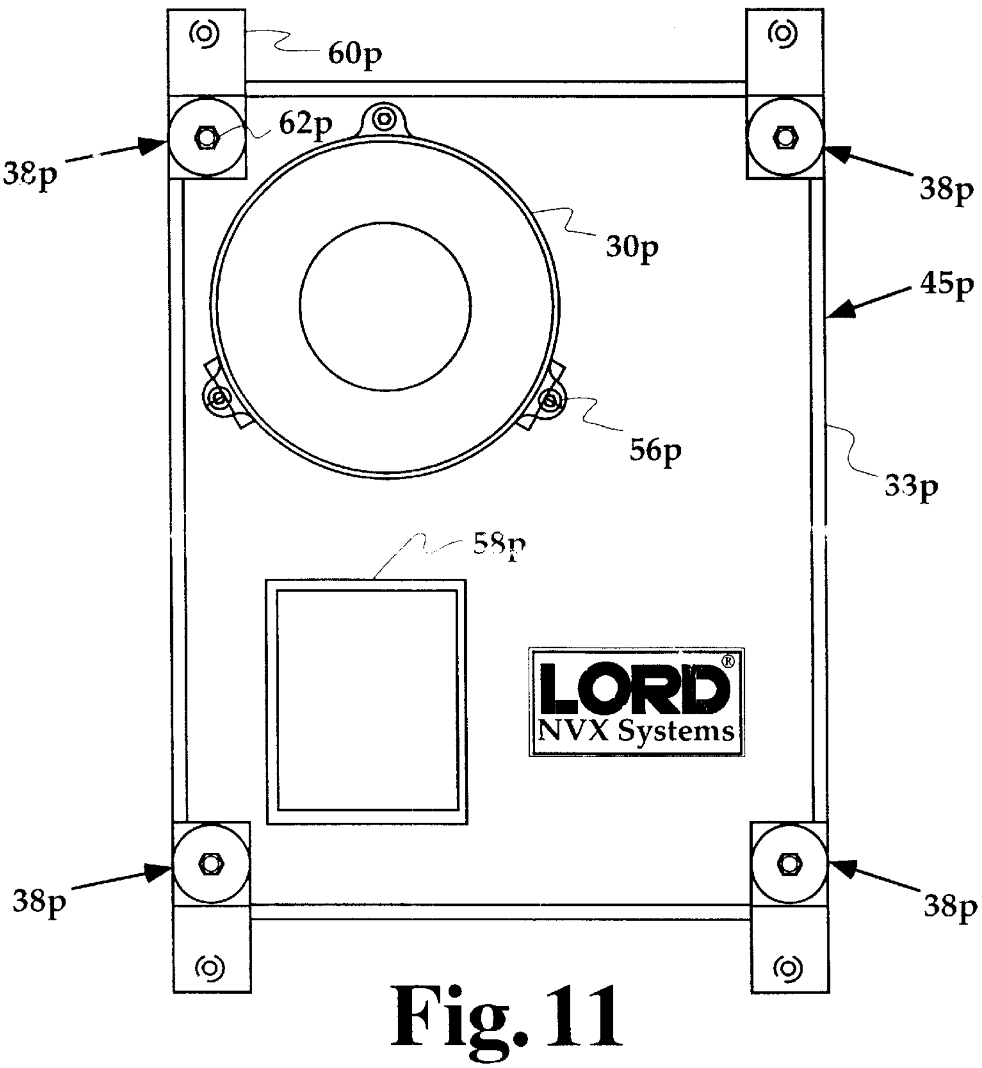
FIG. 11 is a bottom plan view depiction of an inversely-mounted speaker system that includes offset positioning of the speaker and a low-frequency reflex port.

FIG. 11 depicts bottom view of the speaker assembly 45*p* with the enclosure 33*p* soft-mounted with grommet-type mounts 38*p* for flexibly mounting the enclosure 33*p* to the trim (not shown). Preferably, four mounts 38*p* are used with one at each corner. The enclosure 33*p* preferably includes a low-frequency reflex port 58*p*. Further, the speaker 30*p* is preferably offset towards one corner to reduce the acoustic loading on the speaker 30*p* when it is actuated.

In summary, the present invention is directed to an efficient active noise control system for use in a closed structure. The system comprises a reference sensor for deriving a reference signal indicative of a source of disturbance, an error sensor for sensing a residual sound pressure level and providing a signal indicative thereof to an electronic, the electronic controller includes an adaptive filter for providing a canceling signal to a speaker for generating a canceling wave form. In the present invention, the speakers are inversely-mounted in their enclosures and attached directly to the trim of the closed space, thus, providing for more efficient noise cancellation within the space. Preferably, the enclosures are soft-mounted by mounts to protect the speaker components from damage to transient loads applied thereto and to prevent transmission of unwanted vibration to the supporting structure. In another aspect, each speaker assembly and installation preferably performs the function of a planar wave guide and constrains the canceling wave form such that it emanates from the confines of the enclosure in a direction which is substantially parallel to the trim's surface.

Various changes, alternatives and modifications will become apparent to one of ordinary skill in the art following a reading of the foregoing specification. It is intended that all such changes, alternatives, and modifications come within the spirit and scope of the appended claims are to be considered part of the present invention.

What is claimed is:

1. An active control system for a propeller driven aircraft having a fuselage with an interior surface and an exterior surface with trim attached to said interior surface and forming an aircraft cabin therein, said propeller causing propeller wash to impinge on said exterior surface of said fuselage along a plane of action so as to generate a sound pressure level within said aircraft cabin, said system comprising:

(a) means for deriving a reference signal indicative of the propeller wash impinging on said fuselage, said means for deriving said reference signal located adjacent said interior surface of said fuselage and substantially in said plane of action of said propeller wash;

(b) speaker means for generating a canceling wave form for reducing a sound pressure level within said aircraft cabin, said speaker means housed within said aircraft cabin in a box-like enclosure, said enclosure being attached to an interior surface of said trim within said aircraft cabin and inverted within said enclosure such that said canceling wave form is initially primarily directed toward a surface of said trim and then exits into said aircraft cabin in a direction substantially parallel to said surface;

(c) error sensor means located within said aircraft cabin for deriving an error signal indicative of said sound pressure level within said aircraft cabin; and (d) electronic controller means for receiving said reference signal and said error signal, said electronic controller means producing a control signal for driving said speaker means, said control signal being responsive to said error signal so as to drive said speaker to produce a canceling wave form which endeavors to reduce said sound pressure level within said aircraft cabin to a minimum.

2. An active control system of claim 1 wherein said enclosure includes a plurality of escapeways which direct an escape of said canceling wave form from said enclosure in a direction primarily parallel to a surface of said trim, said plurality of escapeways being formed by mounts spacing said enclosure away from said trim.

3. An active control system of claim 1 wherein said trim includes a wall structure having said enclosure flexibly mounted thereto.

4. An active control system of claim 1 wherein said trim includes a floor structure having said enclosure flexibly mounted thereto.

5. An active control system of claim 1 wherein said trim includes a bulkhead structure having said enclosure flexibly mounted thereto.

6. An active control system of claim 1 wherein said enclosure includes means for flexibly mounting to said trim to space said enclosure from said trim and form a plurality of escapeways for said canceling wave form which are parallel to a surface of said trim.

7. An active control system of claim 6 wherein said means for flexibly mounting to said trim are rubber mounts.

8. An active control system of claim 6 wherein said means for flexibly mounting to said trim are rubber grommet-type mounts.

9. An active noise control system for reducing a noise inside an inhabited closed structure which is generated by an external sound and/or vibration source, said closed structure including an interior surface and an exterior surface, and said closed structure having trim attached to said interior surface thereof and forming an interior space, said external sound and/or vibration impinges on said closed structure so as to generate a sound pressure level within said interior space of said closed structure, said active noise control system comprising:

(a) reference sensor means for deriving a reference signal indicative said sound and/or vibration impinging on said closed structure;

(b) inverted speaker means for generating a canceling sound wave form for reducing said sound pressure level within said interior space, said speaker means housed within said closed structure and within a box-like enclosure and inverted within said box-like enclosure such that said canceling sound wave form is primarily directed toward said trim of said closed structure and then exits through an escapeway into said closed structure in a direction substantially parallel to said surface, and said enclosure being soft-mounted to said trim by elastomer mounts which space said enclosure from said trim and form said escapeway which directs said waveform parallel to said trim;

(c) error sensor means located within said closed structure for deriving an error signal indicative of said sound pressure level within said interior space; and (d) electronic controller means for receiving said reference signal and said error signal, said controller means producing a control signal for driving said speaker means to produce said canceling sound wave form, said control signal being responsive to said error signal and striving to drive said sound pressure level within said interior space to a minimum.

10. An active noise control system of claim 9 wherein said interior trim includes one of a wall structure and a floor structure having said enclosure mounted thereto.

11. An active noise control system of claim 9 said elastomer mounts are one of grommet-type mounts and compression mounts.

12. An active control system for reducing a noise inside a inhabited closed structure which is generated by an external noise and/or vibration source, said closed structure including an interior surface and an exterior surface, said closed structure having interior trim attached to said interior surface of said closed structure and forming an interior space, and said external noise and/or vibration impinges on said closed structure so as to generate a sound pressure level within said interior space of said closed structure, said active control system comprising:

(a) reference sensor means for deriving a reference signal indicative said noise and/or vibration impinging on said closed structure;

(b) an array of inverted underseat speaker means for generating canceling sound wave forms for globally reducing said sound pressure level within said interior space, each speaker in said array of inverted underseat speaker means is housed within a box-like enclosure, said enclosure being flexibly mounted by flexible mounts to said trim and each said speaker being inversely-mounted within said enclosure such that said canceling sound wave forms are primarily directed toward said interior trim of said interior space said flexible mounts spacing said enclosure from said trim and forming an escapeway directing said waveform parallel to said trim;

(c) an array of error sensor means located within said interior space for deriving multiple error signals to derive an estimate of a global sound pressure level within said interior space; and (d) controller means for receiving said reference signal and said error signals, said controller means producing control signals for driving said array of inverted underseat speaker means to produce canceling sound wave forms, said control signals being responsive to said error signals and striving to drive said sound pressure level within said interior space to a minimum.

13. An active noise control system of claim 12 wherein said mounts are one of a grommet-type mount and a compression-type mount.

14. An active noise control system of claim 12 wherein said interior space is one of an aircraft cabin and a vehicle passenger compartment.

15. An active noise control system of claim 12 wherein each said speaker in said array is substantially offset into one corner of said box-like enclosure to minimize acoustic loading of said speaker.

16. An active noise control system of claim 12 wherein said enclosures are mounted to a floor structure by four elastomer mounts.

17. An active noise control system of claim 12 wherein each said box like enclosure includes an interior volume and a low-frequency reflex port directed towards said trim to improve low-frequency cancellation, and said speakers are offset to one corner of a bottom face of said box-like enclosure to reduce acoustic loading on said speakers.

18. An active control system for an aircraft having a fuselage, a floor structure, and a closed aircraft cabin therein, said aircraft having a rotating disturbance which generates an annoying sound pressure levels within said aircraft cabin, said system comprising:

(a) means for deriving a reference signal representative of said disturbance;

(b) underseat inverted speaker means for generating a canceling wave form for reducing said annoying sound pressure levels within said closed aircraft cabin, said speaker means housed in a box-like enclosure within said aircraft cabin, said box-like enclosure being spaced from said floor structure such that said canceling wave form is initially directed toward said floor structure and then exits into said aircraft cabin through an escapeway directed parallel to said floor structure;

(c) error sensor means located within said aircraft cabin for deriving an error signal indicative of a residual sound pressure levels within said aircraft cabin; and (d) electronic controller means for receiving said reference signal and said error signal, said electronic controller means producing a control signal for driving said underseat inverted speaker means, said control signal being responsive to said error signal so as to drive said underseat inverted speaker means to produce a canceling wave form which endeavors to reduce said annoying sound pressure levels within said aircraft cabin to a minimum.

* * * * *